(12) United States Patent
Cheng et al.

(10) Patent No.: US 9,101,780 B2
(45) Date of Patent: Aug. 11, 2015

(54) AUTOMATIC EXTERNAL DEFIBRILLATOR FOR IMPLATABLE CARDIAC DEFIBRILLATOR PATIENTS UNDERGOING PROCEDURES INVOLVING ELECTROMAGNETIC INTERFERENCE

(75) Inventors: Alan Cheng, Baltimore, MD (US); Henry Halperin, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 25 days.

(21) Appl. No.: 14/110,499

(22) PCT Filed: Apr. 9, 2012

(86) PCT No.: PCT/US2012/032668
§ 371 (c)(1),
(2), (4) Date: Nov. 25, 2013

(87) PCT Pub. No.: WO2013/106038
PCT Pub. Date: Jul. 18, 2013

(65) Prior Publication Data
US 2014/0088658 A1 Mar. 27, 2014

Related U.S. Application Data

(60) Provisional application No. 61/473,486, filed on Apr. 8, 2011.

(51) Int. Cl.
*A61N 1/00* (2006.01)
*A61N 1/39* (2006.01)
*A61N 1/04* (2006.01)
*A61N 1/08* (2006.01)

(52) U.S. Cl.
CPC .............. *A61N 1/3931* (2013.01); *A61N 1/046* (2013.01); *A61N 1/08* (2013.01); *A61N 1/3925* (2013.01)

(58) Field of Classification Search
CPC ..................................................... A61N 1/3965
USPC ........................................................... 607/5, 6
See application file for complete search history.

(56) References Cited

U.S. PATENT DOCUMENTS

| | | | |
|---|---|---|---|
| 2008/0046015 A1* | 2/2008 | Freeman et al. | 607/6 |
| 2008/0140139 A1 | 6/2008 | Heinrich et al. | |
| 2009/0069857 A1 | 3/2009 | Bucher et al. | |
| 2011/0022105 A9 | 1/2011 | Owen et al. | |
| 2012/0265265 A1* | 10/2012 | Razavi et al. | 607/7 |

FOREIGN PATENT DOCUMENTS

EP 339471 A2 4/1989

* cited by examiner

*Primary Examiner* — Christopher D Koharski
*Assistant Examiner* — Nadia A Mahmood
(74) *Attorney, Agent, or Firm* — Johns Hopkins Technology Transfer

(57) ABSTRACT

An embodiment in accordance with the present invention provides an automatic external defibrillator including an anterior pad designed such that it can be used during an endoscopic or surgical procedure that may generate electromagnetic interference. The anterior pad has a first arm adhered longitudinally along and substantially parallel to a left side of a sternum of the subject and a second arm adhered along a $5^{th}$ intercostal space of the subject. The device also includes a posterior pad. Both the anterior and posterior pads include electrodes for delivering a shock to the subject. The device can also include a wearable component containing sensing electrodes for measuring heart rhythms and a transmitting them to a monitor. The monitor monitors these heart rhythms and alerts the subject or medical care providers to irregularities in the rhythms.

20 Claims, 6 Drawing Sheets

AUTOMATIC EXTERNAL DEFIBRILLATOR FOR IMPLATABLE CARDIAC DEFIBRILLATOR PATIENTS UNDERGOING PROCEDURES INVOLVING ELECTROMAGNETIC INTERFERENCE

CROSS-REFERENCE TO RELATED APPLICATIONS

This application is a 35 U.S.C. 371 U.S. national entry of International Application PCT/US2012/032668 having an international filing date of Apr. 9, 2012 which claims the benefit of U.S. Provisional Application No. 61/473,486, filed Apr. 8, 2011, the content of each of the aforementioned applications is herein incorporated by reference in its entirety.

FIELD OF THE INVENTION

The present invention relates generally to cardiac pacing. More particularly, the present invention relates to an automatic external defibrillator.

BACKGROUND OF THE INVENTION

Electromagnetic interference (EMI) is a commonly encountered during surgical and endoscopic procedures. EMI has the potential to interfere with cardiac electronic devices such as implantable cardioverter defibrillators (ICDs). As a result, currently established guidelines recommend the deactivation of ICDs in some cases. During the period when the ICD is turned off, risks can increase as a result of the lack of immediately available automatic defibrillation.

It would therefore be advantageous to provide an automatic external defibrillator that is configured for use during an endoscopic or surgical procedure, where EMI can be encountered.

SUMMARY OF THE INVENTION

The foregoing needs are met, to a great extent, by the present invention, wherein in one aspect a defibrillator pad includes a first arm to be positioned adjacent and substantially parallel to a left side of a sternum of a subject. The defibrillator pad also includes a second arm to be positioned along an intercostal space of the subject and an electrode positioned along both the first arm and the second arm and configured to deliver an electric shock.

In accordance with an aspect of the present invention, the defibrillator pad is configured for placement on an anterior side of the subject. The intercostal space along which the second arm is positioned, can be the fifth intercostal space. The first arm and the second arm of the defibrillator pad can be operatively connected, and can further be connected to form an obtuse angle. The defibrillator pad can be adhered with a skin-compatible adhesive, which, more particularly, can take the form of a conductive gel adhesive. Additionally, the defibrillator pad can include a safety statement imprinted on a top surface of the pad, stating a warning, such as "DO NOT REMOVE UNTIL ICD REACTIVATED."

In accordance with another aspect of the present invention, an automatic external defibrillator includes a first defibrillator pad having a first electrode configured to deliver an electric shock and a second defibrillator pad having a first arm to be positioned adjacent to and substantially parallel to a left side of a sternum of a subject, a second arm to be positioned along an intercostal space of the subject and a second electrode configured to deliver an electric shock. The device also includes a monitor electrode configured to measure and transmit the subject's heart rhythms and a defibrillator monitor coupled to the monitor electrode and configured to monitor the subject's heart rhythms.

In accordance with yet another aspect of the present invention, the device is further configured to be wearable. The first defibrillator pad can be configured for placement on a posterior side of the subject and the second defibrillator pad for placement on an anterior side of the subject. More particularly, the second arm of the second defibrillator pad can be positioned along a fifth intercostal space. The first arm and the second arm of the defibrillator pad can be operatively connected, and can further be connected to form an obtuse angle. The defibrillator pad and the first and second electrode can be adhered with a skin-compatible adhesive, which, more particularly, can take the form of a conductive gel adhesive. Additionally, the defibrillator pad can include a safety statement imprinted on a top surface of the pad, stating a warning such as "DO NOT REMOVE UNTIL ICD REACTIVATED."

In accordance with still another aspect of the present invention, the automatic external defibrillator can also include a portable monitoring device operatively connected to the defibrillator monitor. The defibrillator monitor can wirelessly transmit data to the portable monitoring device. Additionally, the automatic external defibrillator further, can include a switch for providing immediate shock therapy to the subject.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings.

Therefore, it is to be understood that the presently disclosed subject matter is not to be limited to the specific embodiments disclosed and that modifications and other embodiments are intended to be included within the scope of the appended claims.

An embodiment in accordance with the present invention provides an automatic external defibrillator including an anterior pad designed such that it can be used during an endoscopic or surgical procedure that may generate electromagnetic interference. The anterior pad has a first arm adhered longitudinally along and substantially parallel to a left side of a sternum of the subject and a second arm adhered along a $5^{th}$ intercostal space of the subject. The device also includes a posterior pad. Both the anterior and posterior pads include electrodes for delivering a shock to the subject. The device can also include a wearable component containing sensing electrodes for measuring heart rhythms and a transmitting them to an on-subject monitor. The on-subject monitor monitors these heart rhythms and alerts the subject or medical care providers to irregularities in the rhythms.

Figure 1:
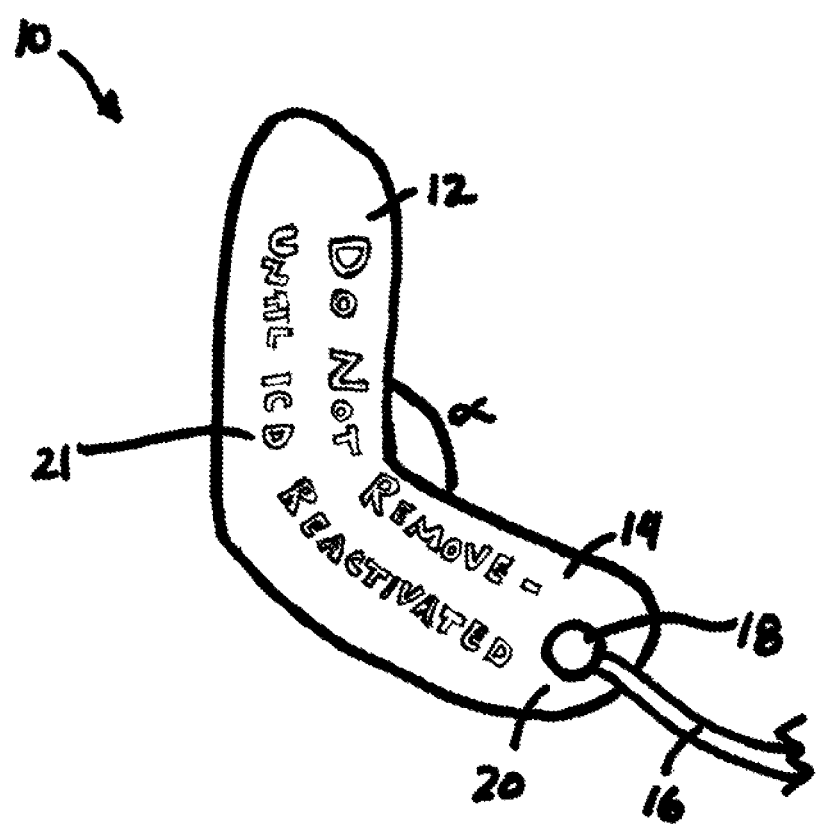
FIG. 1 illustrates a top down view of an anterior defibrillation pad according to an aspect of the invention.

FIG. 1 illustrates a top down view of an anterior defibrillation pad according to an aspect of the invention. As illustrated in FIG. 1, the anterior defibrillation pad 10 includes a first arm 12 and a second arm 14. The first arm 12 and the second arm 14 of the anterior defibrillation pad 10 are operatively connected to one another and define an angle α. The angle α is preferably an obtuse angle, but the anterior pad 10 can also be configured in any other way known to one of skill in the art for delivering a shock to a patient. The angle α is also in a range to allow for the second arm 14 to be positioned along a patient's fifth intercostal space on the patient's left hand side and toward the left mid-axillary line, when the first arm 12 is positioned along and substantially parallel to the patient's sternum on the patient's left hand side.

In order to deliver a shock to a patient, the anterior defibrillation pad includes an electrode (not shown) configured to deliver a suitable shock to a patient. The electrode can extend along both the first arm 12 and the second arm 14, and could possibly also take the form of a first electrode positioned along the first arm 12 and a second electrode positioned along the second arm 14. The electrode of the anterior defibrillator pad 10 is then conductively connected to a capacitor (not shown) via a conductive wire 16 and connector 18. The capacitor can be charged to be ready to provide a shock to the patient and discharged in order to provide that shock. As illustrated in FIG. 1, the connector 18 is positioned on a top surface 20 of the anterior defibrillator pad 10. However, any other suitable positioning for the connector 18 can be used. Also, a bottom surface of the anterior defibrillator pad 10 is coated with an adhesive for securing the pad 10 to the patient's skin. Preferably, the adhesive should be a skin-compatible adhesive, such as a conductive gel adhesive. It should be noted that any suitable adhesive or method of securing the pad 10 to the skin, known to one of skill in the art, can be used.

Additionally, as illustrated in FIG. 1, the anterior defibrillator pad 10 can include a safety statement 21 printed on its surface. For example, in an instance where the anterior defibrillator pad 10 will be placed on a patient because his/her ICD device will be turned off to avoid interference with ECM during a surgical or endoscopic procedure, the anterior defibrillator pad 10 can include a statement such as, "DO NOT REMOVE UNTIL ICD REACTIVATED." This message could be useful in ensuring that the patient does not go home without the ICD being reactivated. Other safety statements could be imprinted on the surface of the anterior defibrillator pad 10, and this example is not meant to be limiting.

Figure 2:
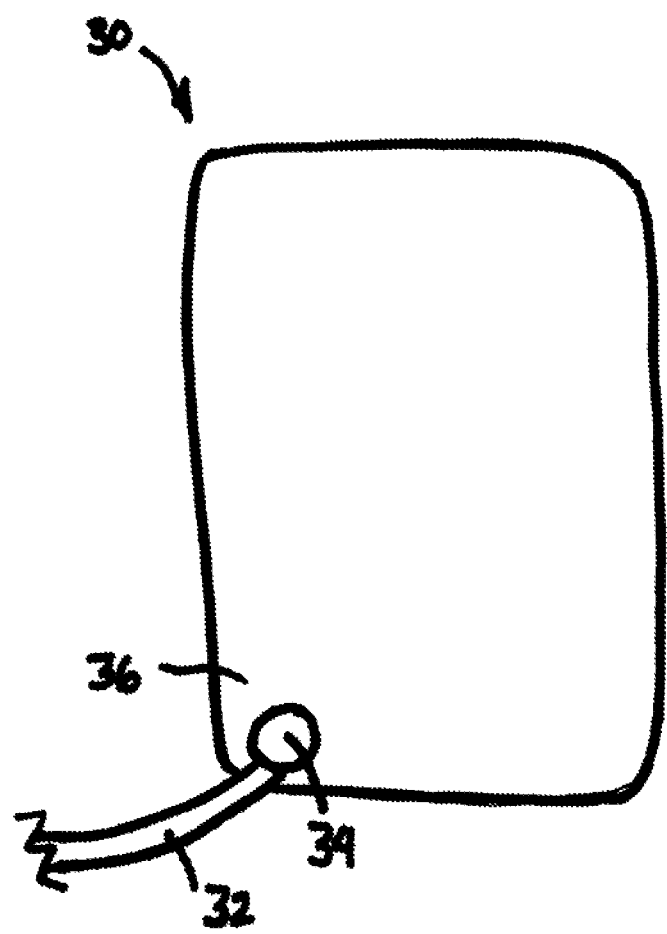
FIG. 2 illustrates a top down view of a posterior defibrillation pad according to an aspect of the invention.

FIG. 2 illustrates a top down view of a posterior defibrillation pad according to an aspect of the invention. As illustrated in FIG. 2, the posterior defibrillator pad 30 has a rectangular shape and is configured to sit just below a scapula on the patient's right hand side. In order to deliver a shock to a patient, the posterior defibrillation pad 30 includes an electrode (not shown) configured to deliver a suitable shock to a patient, in conjunction with the shock delivered via the anterior defibrillation pad, discussed above. The electrode of the posterior defibrillator pad 30 is then conductively connected to the capacitor (not shown), described above, via a conductive wire 32 and connector 34. The capacitor can be charged to be ready to provide a shock to the patient and discharged in order to provide that shock.

As illustrated in FIG. 2, the connector 34 is positioned on a top surface 36 of the posterior defibrillator pad 30. However, any other suitable positioning for the connector 34 can be used. Also, a bottom surface of the posterior defibrillator pad 30 is coated with an adhesive for securing the pad 30 to the patient's skin. Preferably, the adhesive should be a skin-compatible adhesive, such as a conductive gel adhesive. It should be noted that any suitable adhesive or method of securing the pad 30 to the skin, known to one of skill in the art, can be used.

Figure 3:
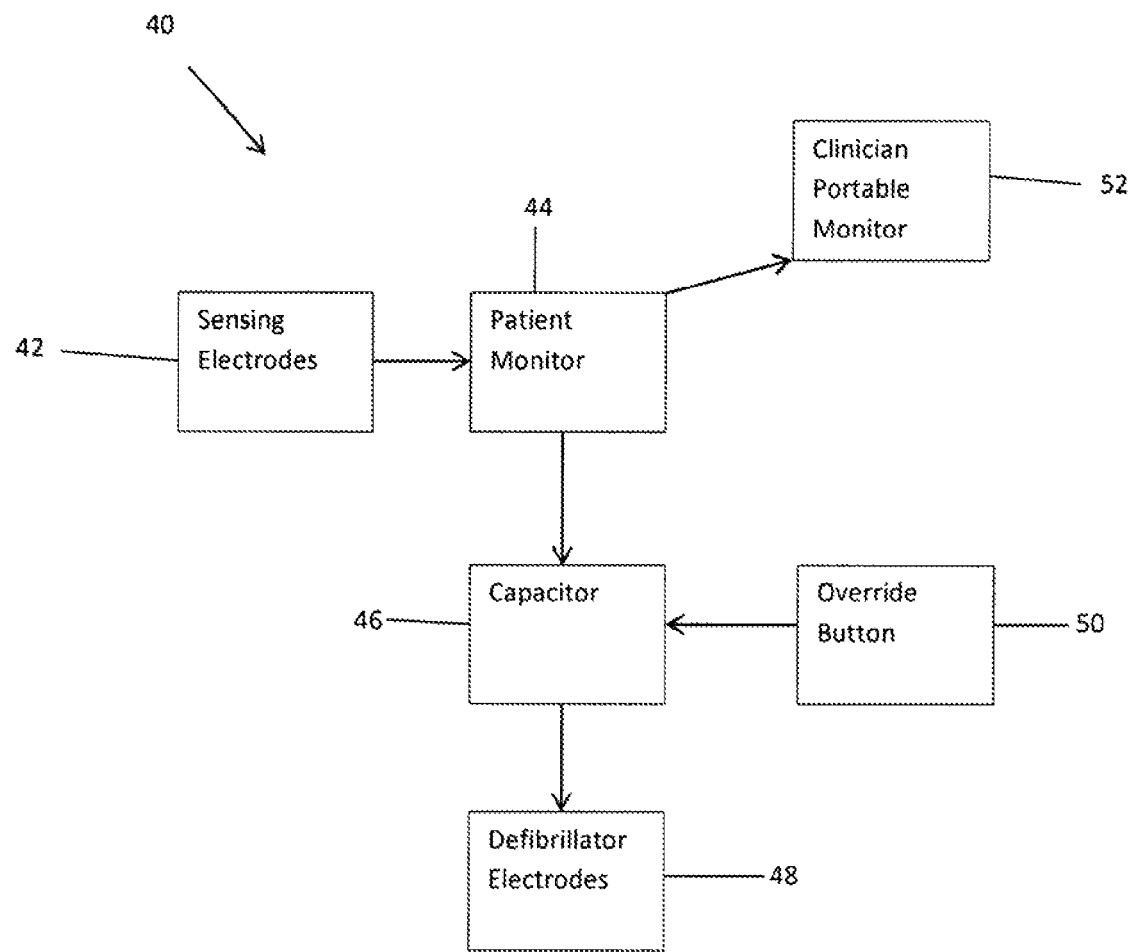
FIG. 3 illustrates a schematic diagram of a defibrillation system according to an aspect of the invention.

FIG. 3 illustrates a schematic diagram of a defibrillation system according to an aspect of the invention. The system 40 illustrated in FIG. 3, includes sensing electrodes 42 that sense the patient's heart rhythms. These sensing electrodes 42 also suppress motion and other extraneous artifact. The sensing electrodes 42 transmit the data collected about the patient's heart rhythms to the patient monitor 44. The patient monitor 44 constantly monitors the heart rhythms transmitted to it from the sensing electrodes 42. The patient monitor 44 is configured to provide no audible alarms until ventricular tachyarrhythmias are detected. When such a ventricular tachyarrythmia is detected, a capacitor 46 is charged. The capacitor 46 can be incorporated into the patient monitor 44 or into a wearable component of the defibrillation system.

Further, as illustrated in FIG. 3, when the capacitor 46 is discharged the accumulated electric current is transmitted to defibrillation electrodes 48, such that a shock is delivered to the patient. The patient monitor 44 can also include an alarm that sounds when a shock will be delivered, in order to warn nearby medical personnel to be clear of the patient. In addition, the patient monitor 44 can include an override button 50 that can be used to immediately deliver a shock to the patient. The system 40 can also include a clinician monitor 52 that provides the clinician with the ability to communicate with the system 40. The clinician monitor 52 can take the form of a smartphone application, an adapter for a smartphone, a standalone unit, or any other suitable device for delivering information to the clinician. The clinician monitor 52 will alert the nurse or ward clinician whenever sustained ventricular arrhythmias are detected and when the capacitor is charging. The clinician monitor 52 also sound an alarm when the system 40 is removed, deactivated, or if the defibrillator electrodes 48 lose contact with the patient's skin.

Figure 4:
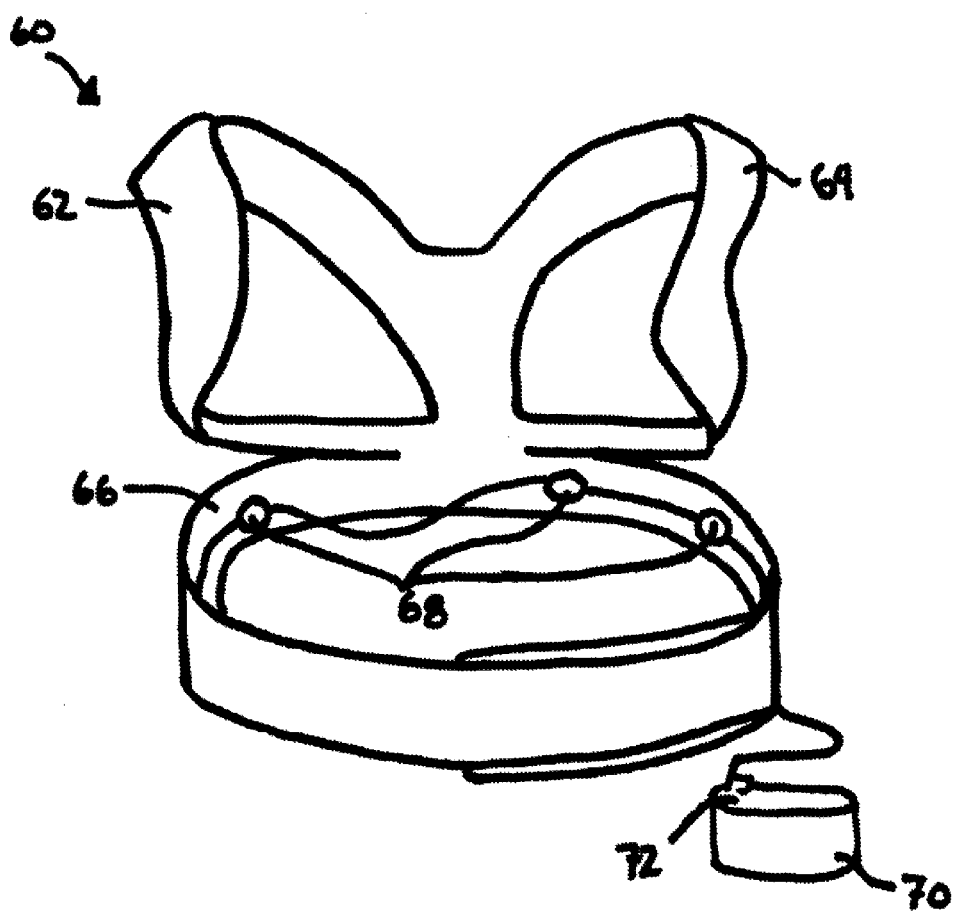
FIG. 4 illustrates a perspective view of a vest and monitor for a defibrillation system according to an aspect of the invention.

FIG. 4 illustrates a perspective view of a vest and monitor for a defibrillation system according to an aspect of the invention. A vest 60, as illustrated in FIG. 4, can be used to hold components of the defibrillation system. The vest 60 includes shoulder straps 62, 64 for securing the vest over the patient's shoulders. Waist strap 66 further secures the vest 60 to the patient and also houses sensing electrodes 68 that sense the patient's heart rhythms. These sensing electrodes 68 also suppress motion and other extraneous artifact. The sensing electrodes 68 transmit the data collected about the patient's heart rhythms to a patient monitor 70. The patient monitor 70 constantly monitors the heart rhythms transmitted to it from the sensing electrodes 68. The patient monitor 70 is configured to provide no audible alarms until ventricular tachyarrhythmias are detected. When such a ventricular tachyarrythmia is detected, a capacitor 72 is charged. The capacitor 72 can be incorporated into the patient monitor 70 or into the vest 60.

Figure 5:
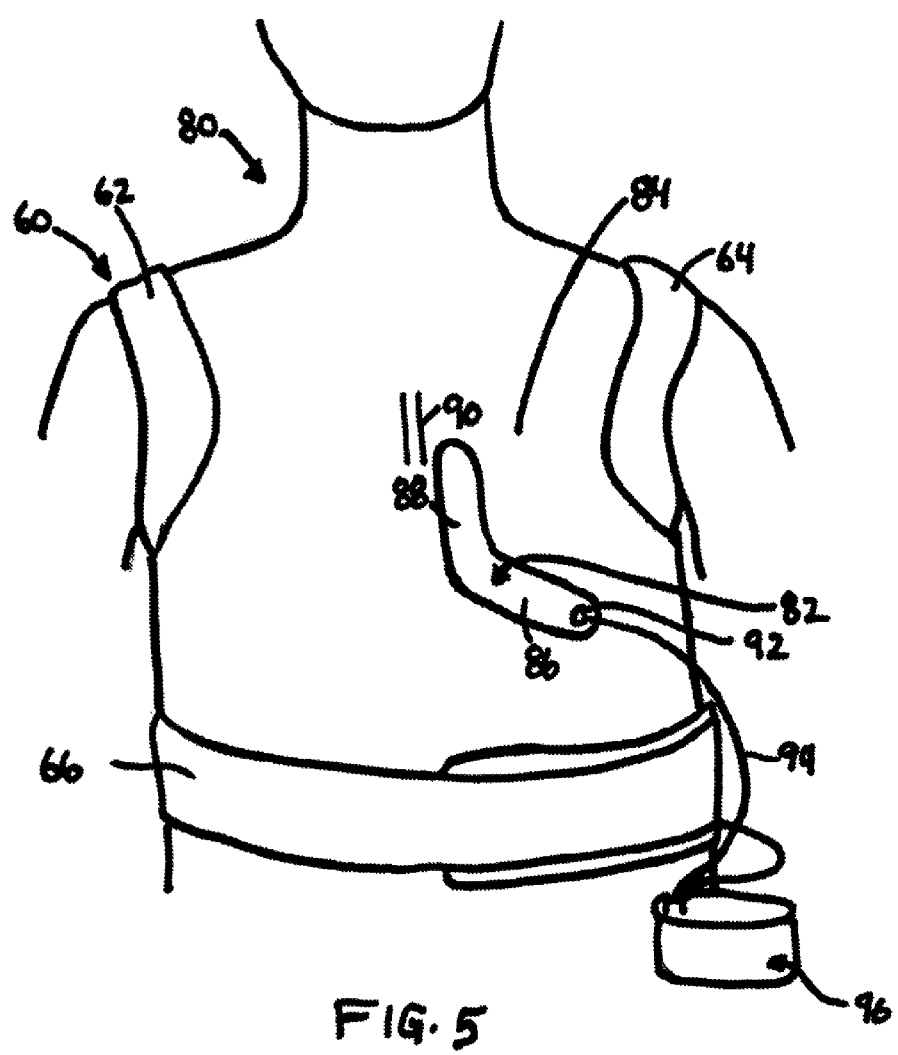
FIG. 5 illustrates an anterior view of a subject wearing an anterior pad, vest, and monitor according to an aspect of the invention.

FIG. 5 illustrates an anterior view of a subject wearing an anterior pad, vest, and monitor according to an aspect of the invention. As illustrated in FIG. 5, a patient 80 wears a vest 60, having shoulder straps 62 and 64 and a waist strap 66. As discussed above, the waist strap 66 houses the sensing electrodes 68 which are kept close to the patient's torso, using the waist strap 66.

Further, as illustrated in FIG. 5, the patient also has an anterior defibrillator pad 82 affixed to his chest 84. More particularly, the anterior defibrillator pad 82 is affixed with a solid, conductive gel such that a second arm 86 is positioned along a patient's fifth intercostal space on the patient's left hand side and toward the left mid-axillary line, when the first arm 88 is positioned along and substantially parallel to the patient's sternum 90 on the patient's left hand side. The anterior defibrillator pad 82 has a connector 92 and a conductive wire 94 that connect it to a capacitor housed within a patient monitor 96. Alternately, the capacitor can be housed within the vest 60.

Figure 6:
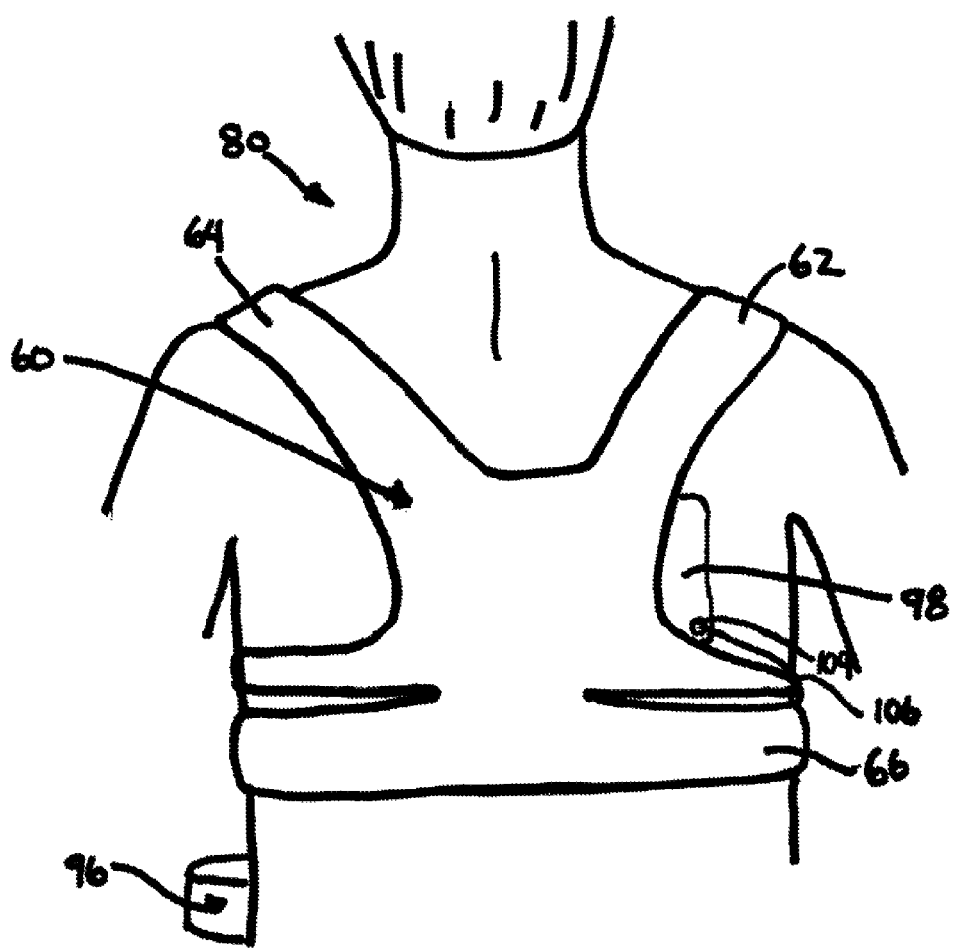
FIG. 6 illustrates a posterior view of a subject wearing a posterior pad, vest, and monitor according to an aspect of the invention.

FIG. 6 illustrates a posterior view of a subject wearing a posterior pad, vest, and monitor according to an aspect of the invention. The patient 80 wears a vest 60, having shoulder straps 62 and 64 and a waist strap 66. As discussed above, the waist strap 66 houses the sensing electrodes 68 which are kept close to the patient's torso, using the waist strap 66.

Further, as illustrated in FIG. 6, the patient 80 also has a posterior defibrillator pad 98 affixed to his back 100. More particularly, the posterior defibrillator pad 98 is affixed with a solid, conductive gel just below a right scapula 102 of the patient 80. The posterior defibrillator pad 98 has a connector 104 and a conductive wire 106 that connect it to a capacitor housed within a patient monitor 96. Alternately, the capacitor can be housed within the vest 60.

While this system has been described for use in during and after a surgical procedure or endoscopy with associated EMI, it need not be limited to this application and could be used any time an automatic external defibrillator is needed known to one of skill in the art. The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A defibrillator pad comprising:
a first arm adapted to be positioned adjacent and parallel to a left side of a sternum of a subject;
a second arm adapted to be positioned along an axis of an intercostal space of the subject, such that the second arm is parallel to the axis of the intercostal space of the subject;
an electrode positioned along both the first arm and the second arm and configured to deliver an electric shock; and
wherein the defibrillator pad is adapted to be positioned entirely to the left side of the sternum of the subject.

2. The defibrillator pad of claim 1 further comprising configuring the pad for placement on an anterior side of the subject.

3. The defibrillator pad of claim 1 wherein the intercostal space comprises a fifth intercostal space.

4. The defibrillator pad of claim 1 further comprising the first arm and the second arm being operatively connected.

5. The defibrillator pad of claim 4 wherein the first arm and the second arm connect to form an obtuse angle, such that the second arm extends along the intercostal space of the subject.

6. The defibrillator pad of claim 1 further comprising a skin-compatible adhesive.

7. The defibrillator pad of claim 6 wherein the skin-compatible adhesive comprises a conductive gel adhesive.

8. The defibrillator pad of claim 1 further comprising a safety statement imprinted on a top surface of the pad.

9. The defibrillator pad of claim 8 wherein the safety statement reads: "DO NOT REMOVE UNTIL ICD REACTIVATED."

10. An automatic external defibrillator comprising:
a first defibrillator pad having a first electrode configured to deliver an electric shock;
a second defibrillator pad having a first arm adapted to be positioned adjacent to and parallel to a left side of a sternum of a subject, a second arm adapted to be positioned along an axis of an intercostal space of the subject, such that the second arm is parallel to the axis of the intercostal space and a second electrode configured to deliver an electric shock wherein the second defibrillator pad is adapted to be positioned entirely to the left side of the sternum of the subject;
a monitor electrode configured to measure and transmit the subject's heart rhythms; and
a defibrillator monitor coupled to the monitor electrode and configured to monitor the subject's heart rhythms.

11. The automatic external defibrillator of claim 10 wherein the device is further configured to be wearable.

12. The automatic external defibrillator of claim 10 wherein the first defibrillator pad is configured for placement on a posterior side of the subject.

13. The automatic external defibrillator of claim 10 further comprising configuring the pad for placement on an anterior side of the subject.

14. The automatic external defibrillator of claim 10 wherein the intercostal space comprises a fifth intercostal space.

15. The automatic external defibrillator of claim 10 further comprising the first arm and the second arm being operatively connected to form an obtuse angle, such that the second arm extends along the intercostal space of the subject.

16. The automatic external defibrillator of claim 10 further comprising a skin-compatible, conductive gel adhesive.

17. The automatic external defibrillator of claim 10 further comprising a safety statement imprinted on a top surface of the pad.

18. The automatic external defibrillator of claim 10 further comprising a portable monitoring device operatively connected to the defibrillator monitor.

19. The automatic external defibrillator of claim 18 wherein the defibrillator monitor wirelessly transmits data to the portable monitoring device.

20. The automatic external defibrillator of claim 10 further comprising a switch for providing immediate shock therapy to the subject.

* * * * *